United States Patent [19]

Inoue et al.

[11] Patent Number: 5,780,634
[45] Date of Patent: Jul. 14, 1998

[54] PROCESS FOR PRODUCING 2-(CARBOXYPHENYL)-4-QUINOLINECARBOXYLIC ACID COMPOUNDS

[75] Inventors: Yoshihisa Inoue; Hajime Ebisu; Naomichi Ishida; Norifumi Nakamura, all of Osaka; Jun Sasaki, Kanagawa; Takashi Okazoe, Kanagawa; Yoshitomi Morizawa, Kanagawa; Arata Yasuda, Kanagawa; Shuzhong Wang, Kanagawa; Tomoko Ito, Kanagawa, all of Japan

[73] Assignees: The Green Cross Corporation, Osaka; Asahi Glass Co., Ltd., Tokyo, both of Japan

[21] Appl. No.: 549,142

[22] Filed: Oct. 27, 1995

Related U.S. Application Data

[63] Continuation-in-part of Ser. No. 55,873, May 4, 1993, Pat. No. 5,478,832, and a continuation-in-part of Ser. No. 541,965, Oct. 10, 1995, Pat. No. 5,665,881, which is a division of Ser. No. 55,873, May 4, 1993, Pat. No. 5,478,832.

[30] Foreign Application Priority Data

| May 8, 1992 | [JP] | Japan | 4-143407 |
| Jun. 10, 1992 | [JP] | Japan | 4-176188 |
| Oct. 27, 1994 | [JP] | Japan | 6-264121 |
| Oct. 27, 1994 | [JP] | Japan | 6-264122 |

[51] Int. Cl.$^6$ .................................. C07D 215/14
[52] U.S. Cl. .................................. 546/173; 546/181
[58] Field of Search .................................. 544/265, 267, 544/268, 277; 546/181, 173, 118

[56] References Cited

U.S. PATENT DOCUMENTS

| 5,371,227 | 12/1994 | Cremer et al. | 546/176 |
| 5,478,832 | 12/1995 | Inoue et al. | 514/266 |

FOREIGN PATENT DOCUMENTS

| 2081537 | 4/1993 | Canada. |
| 0400974 | 12/1990 | European Pat. Off. |
| 0528762 | 2/1992 | European Pat. Off. |
| 0540400 | 5/1993 | European Pat. Off. |

OTHER PUBLICATIONS

Carini et al., "Nonpeptide Angiotensin II Receptor Antagonists: N-[(Benzyloxy)benzyl]imidazoles and Related Compounds as Potent Antihypertensives", *J. Med. Chem.*, 33:5:1330–1336, 1990.

*Primary Examiner*—Matthew V. Grumbling
*Attorney, Agent, or Firm*—Sughrue, Mion, Zinn, Macpeak & Seas, PLLC

[57] ABSTRACT

Quinolin-2-yl benzoic acid compounds which are useful as intermediates of quinoline compounds having angiotensin II antagonist activity prepared by decarboxylating 2-(carboxyphenyl)-4-quinolinecarboxylic acid compounds in which a carboxyl group bonded to a phenyl group may be esterified, while a carboxyl group bonded to a quinoline ring is not esterified, and both rings may have one or more substituents inert to the decarboxylation reaction.

15 Claims, No Drawings

PROCESS FOR PRODUCING 2-(CARBOXYPHENYL)-4-QUINOLINECARBOXYLIC ACID COMPOUNDS

This is a Continuation-In-Part of application Ser. No. 08/055,873 filed 4 May 1993, now U.S. Pat. No. 5,478,832, and a Continuation-In-Part of application Ser. No. 08/541,965 filed 10 Oct. 1995, now U.S. Pat. No. 5,665,881, which is a Division of application Ser. No. 08/055,873 filed May 4, 1993, now U.S. Pat. No. 5,478,832.

FIELD OF THE INVENTION

The present invention relates to a process for producing quinolin-2-yl benzoic acid compounds useful as intermediates of quinoline compounds having angiotensin II antagonism activity. Further, the present invention relates to 2-(carboxyphenyl)-4-quinolinecarboxylic acid compounds useful as starting materials for the production of the above quinolin-2-yl benzoic acid compounds and a process for producing it.

BACKGROUND OF THE INVENTION

Blood pressure is controlled primarily by the sympathetic nerve system and the balance by the pressor and depressor systems. The renin-angiotensin system is a pressor system. In the renin-angiotensin system, renin acts on angiotensinogen to form angiotensin I which subsequently is converted into angiotensin II by the action of an angiotensin converting enzyme. Angiotensin II demonstrates strong angiotonic activity and acts on the adrenal cortex to enhance secretion of aldosterone, thereby increasing the blood pressure. Since angiotensin II acts through an angiotensin II receptor located on the cell membrane, antagonists can be used, in addition to an angiotensin converting enzyme inhibitor, as therapeutic agents for the treatment of hypertension caused by angiotensin II.

Angiotensin II antagonist peptides such as saralasin are known. However, peptides may not be effective when administered orally. Recently, non-peptide angiotensin II antagonists have been reported, for example, in JP-A-56-71074, PCT Application published in Japan as No. 3-501020, JP-A-3-95181, JP-A-3-236377, JP-A-3-271288 and WO93/19060, and their efficacy by oral administration has been confirmed. (The term "JP-A" as used herein means an "unexamined published Japanese patent application").

SUMMARY OF THE INVENTION

As a result of intensive studies to provide a non-peptide compound which has excellent angiotensin II antagonist activity and remains effective when administered orally, it has been found that novel 2-(carboxyphenyl)-4-quinolinecarboxylic acid compounds represented by the following formula (1a) in which $R^{2a}$ is $-CH_2Q$ meet the above requirements. Further, the compounds represented by formula (1a) in which $R^{2a}$ is not $-CH_2Q$ are useful not only as intermediates of the above compounds represented by formula (1a) in which $R^{2a}$ is $-CH_2Q$ but also intermediates of other quinoline derivatives having angiotensin II antagonist activity (for example, compounds represented by formula (2a) in which $R^{2a}$ is $-CH_2Q$).

2-(2-Carboxyphenyl)-4-quinoline carboxylic acid which is represented by formula (1a) in which $R^{2a}$ is a hydrogen atom is described in CA CAS No. =60539-01-7, BEILSTEINs Handbuch, 4.Aufl.2.Erg-Werk, Bd. XXII, 129. However, that compound is not useful as an intermediate of quinoline derivatives having angiotensin II antagonism since it is difficult to introduce $-CH_2Q$.

Further, it has been found that quinolin-2-yl benzoic acid compounds represented by formula (2a) can be produced by decarboxylation of the above-described 2-(carboxyphenyl)-4-quinolinecarboxylic acid.

The quinolin-2-yl benzoic acid compounds demonstrate angiotensin II antagonist activity when $R^{2a}$ is $-CH_2Q$ and those in which $R^{2a}$ is not $-CH_2Q$ are useful as not only intermediates of the above compounds but also intermediates of angiotensin II antagonists represented by formula (2a) in which $-COOR^{32a}$ is substituted by a 1H-tetrazol-5-yl group. That process for producing quinolin-2-yl benzoic acid compounds is advantageous in that the reaction can be carried out easily with high yield as compared to other methods.

The above 2-(carboxyphenyl)-4-quinoline carboxylic acid compound can be produced by reacting an isatin compound with acylbenzoic acid. Those compounds can be used for the production of quinolin-2-yl benzoic acid compounds via decarboxylation, which is advantageous in that the reaction can be carried out easily with high yield as compared to other methods.

The present invention provides a process for producing quinolin-2-yl benzoic acid compounds which comprises decarboxylating 2-(carboxyphenyl)-4-quinolinecarboxylic acid compounds in which a carboxyl group bonded to a phenyl group may be esterified, while a carboxyl group bonded to a quinoline ring is not esterified, and both rings may have substituents inert to the decarboxylation reaction.

The present invention also provides 2-(carboxyphenyl)-4-quinolinecarboxylic acid compounds of formula (1a):

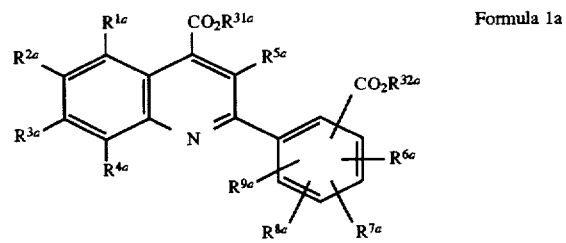

Formula 1a wherein $R^{1a}$, $R^{3a}$, $R^{4a}$, $R^{5a}$, $R^{6a}$, $R^{7a}$, $R^{8a}$ and $R^{9a}$ each independently is a hydrogen atom, a halogen atom, a lower alkyl group, a cyclo lower alkyl group, an aryl group, an aralkyl group, an alkoxy group or $-C_mF_{2m+1}$; $R^{2a}$ is a halogen atom, a lower alkyl group, a cyclo lower alkyl group, an aryl group, an aralkyl group, an alkoxy group, $-C_nF_{2n+1}$ or $-CH_2Q$, wherein Q is a monovalent organic group derived from an organic compound having an $-NH-$ group by eliminating the hydrogen atom bonded to said nitrogen atom; $R^{31a}$ and $R^{32a}$ each independently is a hydrogen atom, a lower alkyl group, an alkenyl group, a cyclo lower alkyl group, an aryl group, or an aralkyl group, and m and n each independently is an integer of from 1 to 6.

Furthermore, the present invention provides a process for producing the above 2-(carboxyphenyl)-4-quinolinecarboxylic acid compounds which comprises reacting an isatin compound of formula (5a):

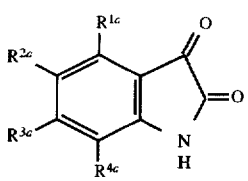

Formula 5a wherein $R^{1a}$, $R^{2a}$, $R^{3a}$ and $R^{4a}$ are as defined above, with an acylbenzoic acid of formula (6a):

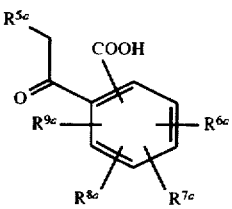

Formula 6a wherein $R^{5a}$, $R^{6a}$, $R^{7a}$, $R^{8a}$ and $R^{9a}$ are as defined above.

DETAILED DESCRIPTION OF THE INVENTION

The term "lower" as used herein with regard to organic groups indicates that each group has 1 to 6 carbon atoms. Suitable examples of the lower alkyl groups include methyl, ethyl, propyl, isopropyl, butyl, isobutyl, t-butyl, pentyl and hexyl groups.

The cyclo lower alkyl groups are cycloalkyl groups having 3 to 6 carbon atoms which constitute the ring, with typical examples including cyclopropyl, cyclobutyl, cyclopentyl and cyclohexyl groups.

The halogen atoms include fluorine, chlorine, bromine and iodine.

The aryl groups are monovalent aromatic hydrocarbon radicals and preferably is a phenyl group or derivatives thereof. Suitable examples thereof include phenyl, tolyl and p-halophenyl.

The aralkyl groups are alkyl groups substituted with aryl groups, in which the alkyl groups may preferably have 1 to 4 carbon atoms, with typical examples including benzyl, benzhydryl, trityl and phenetyl groups.

The alkoxy groups are preferably lower alkoxy groups, more preferably those having 1 to 4 carbon atoms, with typical examples including methoxy, ethoxy, propoxy and butoxy groups.

The alkenyl groups are preferably lower alkenyl groups, more preferably those having 2 to 4 carbon atoms, which may be linear or branched, with typical examples including vinyl, allyl, 1-propenyl, isopropenyl and 1-butenyl groups.

2-(Carboxyphenyl)-4-quinolinecarboxylic acid compounds of formula (1a)

Preferably, $R^{1a}$, $R^{3a}$, $R^{4a}$, $R^{5a}$, $R^{6a}$, $R^{7a}$, $R^{8a}$ and $R^{9a}$ each independently is a hydrogen atom, a halogen atom or a lower alkyl group, a hydrogen atom or an alkyl group having 1 to 4 carbon atoms being particularly preferred. A chlorine atom or a fluorine atom is preferred as a halogen atom. It is most preferable that $R^{1a}$, $R^{3a}$, $R^{4a}$ and $R^{5a}$ each is a hydrogen atom. Preferably, $R^{6a}$, $R^{7a}$, $R^{8a}$ and $R^{9a}$ each is a hydrogen atom or at least one of them is a halogen atom, preferably a chlorine atom, while the others are hydrogen atoms. The group —COOR$^{32a}$ preferably is located at the 2-position of the benzene ring. $R^{2a}$ is preferably a lower alkyl group or —CH$_2$Q, more preferably a methyl group or —CH$_2$Q. More specifically, a methyl group serves as a connecting group between an imidazole ring, an imidazopyridine ring or the like and the quinoline skeleton in a quinoline angiotensin II antagonist and —CH$_2$Q itself preferably compromises an imidazole ring, imidazopyridine ring or the like.

Q is a monovalent organic group derived from an organic compound having an —NH— group by eliminating the hydrogen atom bonded to said nitrogen atom. The organic compound having an —NH— group is preferably a heterocyclic compound wherein the nitrogen atom in the —NH— group constitutes the ring. The heterocyclic compound may be a condensed one. The organic compound having an —NH— group may be an aliphatic amine compound, an alicyclic amine compound or an aromatic amine compound, having at least one primary or secondary amino group.

Preferable examples of Q include residues of heterocyclic compounds such as residues of substituted imidazole compounds and substituted imidazopyridine compounds. For example, Q is preferably a substituted 1H-imidazol-1-yl group represented by formula (3a), more preferably a substituted 3H-imidazo|4,5-b|pyridin-3-yl group represented by formula (4a).

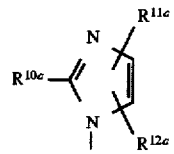

Formula 3a

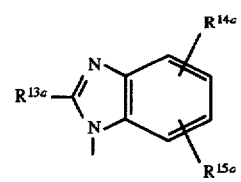

Formula 4a wherein $R^{10a}$ and $R^{13a}$ each independently is a lower alkyl group, a halo lower alkyl group, a cyclo lower alkyl group, an alkenyl group, an alkoxy group, an alkoxy lower alkyl group, or an alkylthio group; $R^{11a}$ and $R^{12a}$ may be the same or different and each independently is a hydrogen atom, a halogen atom, $C_jF_{2j+1}$—, —(CH$_2$)$_p$R$^{20a}$, —(CH$_2$)$_r$COR$^{21a}$, or —(CH$_2$)$_s$NR$^{22a}$COR$^{23a}$; $R^{14a}$ and $R^{15a}$ may be the same or different and each independently is a hydrogen atom, a halogen atom, a lower alkyl group, a halo lower alkyl group, a cyclo lower alkyl group, an alkenyl group, an alkoxy group, $C_jF_{2j+1}$—, —(CH$_2$)$_q$R$^{24a}$ or —(CH$_2$)$_s$COR$^{25a}$; $R^{20a}$ and $R^{24a}$ each independently is a hydroxyl group or an alkoxy group; $R^{21a}$ and $R^{25a}$ each independently is a hydrogen atom, a lower alkyl group or an alkoxy group; $R^{22a}$ is a hydrogen atom or a lower alkyl group; $R^{23a}$ is a hydrogen atom, a lower alkyl group or an alkoxy group; i and j each independently is an integer of from 1 to 6; p and q each independently is an integer of from 1 to 4; r and s each independently is 0 or an integer of from 1 to 4; and t is 0 or an integer of from 1 to 4.

Preferably, $R^{10a}$ and $R^{13a}$ each independently is a lower alkyl group, $R^{12a}$ is —(CH$_2$)$_p$R$^{20a}$, wherein $R^{20a}$ is a hydroxy group and p is 1, or —(CH$_2$)$_r$COR$^{21a}$, wherein $R^{21a}$ is a hydrogen atom or a lower alkoxy group and r is 0 or 1, $R^{14a}$ and $R^{15a}$ may be the same or different and each independently is a hydrogen atom, a lower alkyl group, —(CH$_2$)$_q$R$^{24a}$, wherein $R^{24a}$ is a hydroxy group and q is 1, or —(CH$_2$)$_s$COR$^{25a}$, wherein $R^{25a}$ is a hydrogen atom or a lower alkoxy group and s is 0 or 1.

Preferably, $R^{31a}$ and $R^{32a}$ each independently is a hydrogen atom or a lower alkyl group. An alkyl group having 1 to 4 carbon atoms, such as a methyl group, is preferable as a lower alkyl group. Preferably, $R^{31a}$ is a hydrogen atom and $R^{32a}$ is a hydrogen atom or a lower alkyl group for the purpose of decarboxylation as described below.

A preferable compound of formula (1a) is 2-(2-carboxyphenyl)-6-methyl-4-quinoline-carboxylic acid, its mono(lower alkyl)ester or di(lower alkyl)ester. As a lower alkyl group, a methyl group is preferred. Preferable compounds are those having —$CH_2Q$, wherein Q is a substituted 1H-imidazol-1-yl group or a substituted 3H-imidazo|4,5-b| pyridin-3-yl group, at the 6-position in place of the methyl group.

Decarboxylation of 2-(carboxyphenyl)-4-quinolinecarboxylic acid compounds

Quinolin-2-yl benzoic acid compounds can be obtained by decarboxylating the above-described 2-(carboxyphenyl)-4-quinolinecarboxylic acid compounds. The quinoline ring and the benzene ring of 2-(carboxyphenyl)-4-quinolinecarboxylic acid compounds may have substituents inert to the decarboxylation reaction. Each ring may have two or more substituents which may be the same or different. A preferable example of the 2-(carboxyphenyl)-4-quinolinecarboxylic acid compounds are those represented by formula (1a).

A carboxyl group bonded to the quinoline ring should not be substituted when subjected to the decarboxylation reaction, while a carboxyl group bonded to the benzene ring may be substituted. In formula (1a), $R^{31a}$ is a hydrogen atom and $R^{32a}$ is a hydrogen atom or an organic group such as a lower alkyl group, preferably a methyl group.

A compound of formula (1a) in which $R^{31a}$ is a hydrogen atom and $R^{32a}$ is a lower alkyl group (e.g., 2-(2-alkoxycarbonylphenyl)-6-methyl-4-quinolinecarboxylic acid) can be obtained by diesterifying the compound of formula (1a) in which $R^{31a}$ and $R^{32a}$ each is a hydrogen atom and selectively hydrolyzing the ester residue bonded to the quinoline ring.

Another, and possibly simpler method is as follows. A carboxyl group bonded to the quinoline ring can be decarboxylated selectively by subjecting the compound of formula (1a) in which $R^{31a}$ and $R^{32a}$ each is a hydrogen atom (e.g., 2-(2-carboxyphenyl)-6-methyl-4-quinolinecarboxylic acid) to decarboxylation directly. The desired product can be obtained economically in a high yield by such a direct decarboxylation method as compared with conventional methods.

The quinolin-2-yl benzoic acid compounds represented by formula (2a) can be obtained by decarboxylating the 2-(carboxyphenyl)-4-quinolinecarboxylic acid compounds represented by formula (1a).

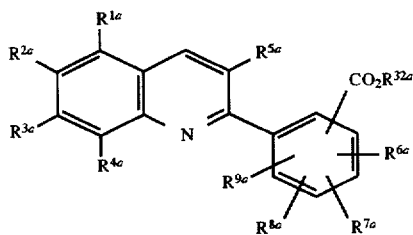

Formula 2a wherein $R^{1a}$ through $R^{9a}$ and $R^{32a}$ are as defined above. Preferable examples of those groups are also the same as described above. Decarboxylation of 2-(carboxyphenyl)-4-quinolinecarboxylic acid compounds in which $R^{2a}$ is a hydrogen atom previously had not been possible.

Preferable examples of the compounds represented by formula (2a) are 2-(6-methylquinolin-2-yl)benzoic acid and lower alkyl esters thereof. A methyl group is preferable as a lower alkyl group. Preferable compounds are those having a —$CH_2Q$ group at the 6-position in place of a methyl group, wherein Q is a substituted 1H-imidazol-1-yl or a substituted 3H-imidazo|4,5-b|pyridin-3-yl group.

A 2-carboxyphenyl-4-quinolinecarboxylic acid can be decarboxylated by heating an appropriate solvent. A decarboxylation accelerator such as an appropriate acid or base may be used together with the solvent. However, it is unnecessary to use a decarboxylation accelerator or an acid. The heating temperature preferably ranges from 100° to 250° C., more preferably from 130° to 200° C. The reaction time ranges from 0.1 to 10 hours, preferably from 0.5 to 2 hours.

It is preferable to use a solvent having a boiling point of from 100° to 250° C., more preferably from 150° to 230° C. Suitable examples of the solvent include diphenyl ether, N,N-dimethylacteamide, quinoline, o-dichlorobenzene and xylene. It is preferable to use from 10 to 10,000 ml of the solvent per mol of the 2-carboxyphenyl-4-quinolinecarboxylic acid.

The acid to be used as the decarboxylation accelerator may be selected from among organic acids, mineral acids and Lewis acids, which are highly stable to heat. Suitable examples of the acid include benzenesulfonic acid, p-toluenesulfonic acid, camphorsulfonic acid, hydrochloric acid, sulfuric acid, boric acid, copper oxide, boron trifluoride and acidic alumina. It is particularly preferable to use conc. sulfuric acid.

The base to be used as the decarboxylation accelerator may be selected from among organic amines, organic acid salts and alkalis. Suitable examples thereof include triethylamine, diisopropylamine, N,N-dimethylaniline, sodium acetate, potassium acetate, sodium methoxide, sodium ethoxide, sodium phenoxide, sodium hydroxide, potassium hydroxide, calcium hydroxide, magnesium hydroxide, sodium carbonate, potassium carbonate, sodium hydrogencarbonate, calcium carbonate and basic alumina.

The decarboxylation accelerator is used in an amount of preferably from 0.0001 to 100 mols, more preferably 0.001 to 10 mols, per mol of the 2-carboxyphenyl-4-quinolinecarboxylic acid.

After allowing to cool to room temperature, the reaction mixture thus obtained is poured into water cooled with ice. Then the mixture is made alkaline by adding an appropriate base such as sodium carbonate or sodium hydroxide. The aqueous layer is washed with an appropriate organic solvent such as dichloromethane or toluene and acidified with diluted hydrochloric acid. The precipitate thus formed is collected by filtration or extraction with an appropriate organic solvent such as dichloromethane or ethyl acetate. Thus the desired quinolin-2-yl benzoic acid can be obtained. The 2-carboxyphenyl-4-quinolinecarboxylic acid in which $R^{32a}$ is a hydrogen atom can be produced by decarboxylating the corresponding compound in which $R^{32a}$ is not a hydrogen atom and hydrolyzing the resulting product.

Production of 2-(carboxyphenyl)-4-quinolinecarboxylic acid compounds

The 2-(carboxyphenyl)-4-quinolinecarboxylic acid compounds represented by formula (1a) in which $R^{31a}$ and $R^{32a}$ are both hydrogen atoms can be produced by reacting isatin compounds represented by formula (5a) with acyl benzoic acid compounds represented by formula (6a). Thereafter, the resulting products are subjected to esterification to obtain a compound in which at least one of $R^{31a}$ and $R^{32a}$ is not a hydrogen atom.

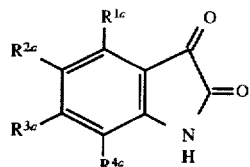

Formula 5a

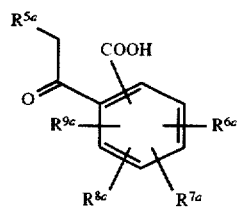

Formula 6a wherein $R^{1a}$ through $R^{9a}$, $R^{31a}$ and $R^{32a}$ are as defined above. Preferable examples of those groups are also the same as described above.

The reaction can be carried out by reacting the isatin compounds with the acyl benzoic acid compounds in a reaction medium in the presence of a base. For example, both compounds are allowed to react in a basic aqueous solution under heating. As a base, alkaline metal hydroxides such as sodium hydroxide or potassium hydroxide are preferred. A preferable reaction medium is water. The acylbenzoic acid compounds are used preferably in an amount of 0.5 to 10 mols, particularly 0.5 to 2 mols, per mol of the isatin compounds. The base preferably is used in an amount of 1 to 4 mols, particularly 2 to 3 mols, per mol of the acylbenzoic acid compounds. The reaction can be carried out at a temperature of from 50° C. to the reflux temperature of the reaction medium, particularly 80° C. to the reflux temperature, for 0.5 to 10 hours, suitably 1 to 3 hours.

The purification methods after the reaction are not limited particularly, but the following method preferably is used. After allowing to cool to room temperature, the reaction mixture is poured into water cooled with ice, the aqueous layer is washed with an organic solvent such as ether and acidified with diluted hydrochloric acid to form a precipitate, and the precipitate is collected by filtration to obtain the desired product.

For example, 5-methylisatin is reacted with 2-acetylbenzoic acid as described above to give 2-(2-carboxyphenyl)-6-methyl-4-quinolinecarboxylic acid. 2-(Carboxyphenyl)-4-quinolinecarboxylic acid having —$CH_2Q$ at the 6-position can be obtained by reacting an isatin compound having —$CH_2Q$ at the 5-position with an acylbenzoic acid.

The isatin represented by formula (5a) can be obtained by reacting an aniline compound having $R^{2a}$ at the para-position with chloral hydrate and a hydroxylamine hydrochloride in an acidic aqueous solution to form isonitrosoacetanilide, followed by cyclization, for example, by Sandmeyer's method. 5-Methylisatin can be produced from p-toluidine by that method. The isatin compounds having —$CH_2Q$ at the 5-position can be obtained from an aniline compound having —$CH_2Q$ at the para-position.

Compounds in which $R^{2a}$ is a methyl group can be made into those in which $R^{2a}$ is —$CH_2Q$ by converting the methyl group into —$CH_2L$, wherein L is a leaving group, and then reacting L with QH to form —$CH_2Q$. The leaving group L is a halogen atom (for example, chlorine, bromine, iodine), a methanesulfonyloxy group or a p-toluenesulfonyloxy group. Alternatively, when L is chlorine, bromine or iodine, the methyl group can be reacted with N-chlorosuccinimide, N-bromosuccinimide or N-iodosuccinimide in the presence of a radical initiator such as azobisiso-butyronitrile or dibenzoyl peroxide to form —$CH_2L$. The reaction can be carried out with the use of light irradiation in place of a radical initiator. The compound having —$CH_2L$ can be converted to that having —$CH_2Q$ by reacting it with QH in the presence of a base, such as sodium hydride, sodium carbonate, potassium carbonate or sodium methoxide, in a nonprotic solvent, such as N,N-dimethylformamide, N,N-dimethylacetamide, tetrahydrofuran or dioxane, at a temperature of from 0° C. to the reflux temperature of the solvent.

The aniline compound having —$CH_2Q$ at the para-position can be obtained by subjecting the corresponding nitrobenzene compound to hydrogen reduction. The nitrobenzene compound can be produced by reacting a nitrobenzene compound having —$CH_2L$ at the para-position with an amine represented by QH in accordance with the above-described method. Hydrogen reduction of the nitrobenzene compound can be carried out in a hydrogen atmosphere in the presence of a catalytic hydrogenation catalyst, such as palladium or Raney nickel. Alternatively, the same reaction can be performed using a metallic hydrogenation agent instead of the above-mentioned catalytic hydrogenation catalyst.

The following examples are provided to further illustrate the present invention. It is to be understood, however, that the examples are for purpose of illustration only and are not intended as a definition of the limits of the present invention.

EXAMPLE 1

Synthesis of 5-methylisatin

An aqueous solution (222 ml) containing 16.7 g (0.10 mol) of chloral hydrate was mixed with 243 g of sodium sulfate, an aqueous solution (56.0 ml) containing 10.0 g (93.3 mmol) of p-toluidine and 9.56 ml of concentrated hydrochloric acid and an aqueous solution (242 ml) containing 20.5 g (0.29 mol) of hydroxylamine hydrochloride in that order and the resulting mixture was heated under reflux with stirring for 30 minutes. After cooling to room temperature, the mixture was filtered with suction to collect a yellowish-brown precipitate. The precipitate was dissolved in 500 ml of a 1.5N sodium hydroxide solution and neutralized with 2M hydrochloric acid. The resulting mixture was filtered and the filtrate was acidified with 2M hydrochloric acid. The thus precipitated isonitroso compound was collected by filtration and washed with iced water followed by drying. The dried product was added to 62 g of concentrated sulfuric acid which had been heated to 60° C. over 40 minutes and the mixture was heated further at 75° C. for 10 minutes. After cooling to room temperature, the resulting mixture was poured into 160 ml of iced water followed by filtration to obtain 10.0 g of 5-methylisatin. NMR (270 MHz, Acetone-$d_6$):

δ 9.9 (bs,1H); 6.9–7.5 (m, 3H); 2.3 (s, 3H)

EXAMPLE 2

Synthesis of 2-(2-carboxyphenyl)-6-methyl-4-quinolinecarboxylic acid

To 9.93 ml of water were added 10.0 g (62.1 mmol) of 5-methylisatin obtained in Example 1 and 4.96 g (0.12 mol) of sodium hydroxide. 10.2 g (62.1 mmol) of 2-acetylbenzoic acid was added thereto and the mixture was heated to 90° C. under reflux. The mixture was heated further at 115° C. for one hour after the reaction became mild. Thereafter, the mixture was allowed to cool to room temperature and poured into 200 g of iced water. The aqueous layer was washed with ether and acidified with 2M hydrochloric acid. The formed precipitate was collected by filtration to obtain 6.55 g of 2-(2-carboxyphenyl)-6-methyl-4-quinolinecarboxylic acid. NMR (270 MHz, Acetone-$d_6$):

δ 7.70–8.70 (m, 8H); 2.66 (s, 3H)

EXAMPLE 3

Synthesis of methyl 2-(2-methoxycarbonylphenyl)-6-methyl-4-quinolinecarboxylate 2.77 g (9.03 mmol) of 2-(2-carboxyphenyl)-6-methyl-4-quinolinecarboxylic acid obtained in Example 2 was suspended in 10 ml of methanol. 1.3 ml (18 mmol) of thionyl chloride was added thereto with maintaining the mixture at −10° C. and the mixture was stirred for 24 hours. After concentrated under reduced pressure, the residue was purified by flash silica gel chromatography using chloroform to obtain 377 mg of methyl 2-(2-methoxycarbonylphenyl)-6-methyl-4-quinolinecarboxylate. NMR (270 MHz, CDCl$_3$):

δ 7.49–8.56 (m, 8H); 4.04 (s, 3H); 3.62 (s, 3H); 2.60 (s, 3H)

EXAMPLE 4

Synthesis of 2-(2-methoxycarbonylphenyl)-6-methyl-4-quinolinecarboxylic acid

In 2 ml of methanol were dissolved 377 mg (1.23 mmol) of methyl 2-(2-methoxycarbonylphenyl)-6-methyl-4-quinolinecarboxylate obtained in Example 3 and 49 mg (1.2 mmol) of sodium hydroxide. 3 ml of water were added thereto and the resulting mixture was stirred for 24 hours. After concentrated under reduced pressure, water was added to the residue, the aqueous layer was acidified and extracted with ethyl acetate. The organic layer was dried over magnesium sulfate followed by distillation under reduced pressure. The resulting residue was purified by flash silica gel chromatography using a mixed solvent of chloroform and methanol (70/1) to obtain 267 mg of 2-(2-methoxycarbonyl-phenyl)-6-methyl-4-quinolinecarboxylic acid. NMR (270 MHz, CD$_3$OD):

δ 7.70–8.58 (m, 8H); 3.60 (s, 3H); 2.59 (s, 3H)

EXAMPLE 5

Synthesis of methyl 2-(6-methylquinolin-2-yl)benzoate 267 mg (0.831 mmol) of 2-(2-methoxycarbonylphenyl)-6-methyl-4-quinolinecarboxylic acid obtained in Example 4 was dissolved in 4.0 ml of diphenyl ether and heated at 225° C. for 10 minutes. After allowing the mixture to cool to room temperature, purification was carried out by flash silica gel chromatography using a mixed solvent of hexane and ethyl acetate (10/1) to obtain 154 mg of methyl 2-(6-methylquinolin-2-yl)benzoate. NMR (270 MHz, CDCl$_3$):

δ 7.47–8.13 (m, 9H); 3.63 (s, 3H); 2.56 (s, 3H)

EXAMPLE 6

Synthesis of 2-(6-methylquinolin-2-yl)benzoic acid 7.08 g (25.5 mmol) of methyl 2-(6-methylquinolin-2-yl)benzoate obtained in Example 5 was suspended in 75 ml of methanol and 35 ml of water in which 3.06 g (76.6 mmol) of sodium hydroxide was dissolved was added thereto. After heating at 60° C. for 3 hours, the reaction mixture was concentrated under reduced pressure and 200 ml of water was added to the residue. The resulting solution was acidified with 2N hydrochloric acid and the thus formed precipitate was collected by filtration. The precipitate was washed with water and dried to obtain 2-(6-methylquinolin-2-yl)benzoic acid. NMR (270 MHz, CD$_3$OD):

δ 7.6–8.3 (m, 9H); 2.58 (s, 3H)

EXAMPLE 7

Synthesis of methyl 6-[(2-butyl-4-chloro-5-formyl-1H-imidazol-1-yl)methyl]-2-(2-methoxycarbonylphenyl)-4-quinolinecarboxylate To 540 mg (1.610 mmol) of methyl 2-(2-methoxycarbonylphenyl)-6-methyl-4-quinolinecarboxylate obtained in Example 3 were added 4 ml of carbon tetrachloride and then 315 mg (1.77 mmol) of N-bromosuccinimide and 8.7 mg (0.053 mmol) of azobisisobutyronitrile. The mixture was heated under reflux for one hour and concentrated under reduced pressure. The residue was dissolved in dichloro-methane and washed with water. The organic layer was dried over magnesium sulfate and filtered. The filtrate was concentrated under reduced pressure.

The thus obtained residue was dissolved in 2 ml of N,N-dimethylformamide. To the solution were added 44.6 mg (0.239 mmol) of 2-butyl-4-chloro-1H-imidazol-5-carbaldehyde and 36.3 mg of potassium carbonate. The resulting mixture was stirred at room temperature for 24 hours followed by filtration. The filtrate was concentrated under reduced pressure and the residue was purified by flash silica gel chromatography using a mixed solvent of hexane and ethyl acetate (5/1 to 4/1) to obtain 65.5 mg of methyl 6-[(2-butyl-4-chloro-5-formyl-1H-imidazol-1-yl)methyl]-2-(2-methoxycarbonylphenyl)-4-quinolinecarboxylate. NMR (270 MHz, CDCl$_3$):

δ 9.8 (s, 1H); 7.5–8.5 (m, 8H); 5.8 (s, 2H); 4.0 (s, 3H); 3.6 (s, 3H); 2.7 (t, J=8 Hz, 2H); 1.7 (m, 2H); 1.4 (m, 2H); 0.8 (t, J=7 Hz, 3H)

EXAMPLE 8

Synthesis of methyl 6-[(2-butyl-4-chloro-5-hydroxymethyl-1H-imidazol-1-yl)methyl]-2-(2-methoxycarbonylphenyl)-4-quinolinecarboxylate 65.5 mg (0.126 mmol) of methyl 6-[(2-butyl-4-chloro-5-formyl-1H-imidazol-1-yl)methyl]-2-(2-methoxycarbonylphenyl)-4-quinolinecarboxylate obtained in Example 7 was dissolved in a mixed solvent of 2 ml of tetrahydrofuran and 2 ml of methanol and the mixture was stirred. After adding 5.24 mg (0.139 mmol) of sodium borohydride, the reaction mixture was allowed to react at room temperature for one hour. Then, the reaction mixture was concentrated under reduced pressure and dichloromethane was added to the residue followed by washing with a saturated sodium chloride solution. The organic layer was dried over magnesium sulfate and filtered. The filtrate was concentrated under reduced pressure to obtain 50.6 mg of methyl 6-[(2-butyl-4-chloro-5-hydroxymethyl-1H-imidazol-1-yl)methyl]-2-(2-methoxycarbonyl-phenyl)-4-quinolinecarboxylate. NMR (270 MHz, CDCl$_3$):

δ 7.4–8.4 (m, 8H); 5.4 (s, 2H); 4.5 (bs, 2H); 4.0 (s, 3H); 3.6 (s, 3H); 2.8 (bs, 1H); 2.6 (t, J=8 Hz, 2H); 1.6 (m, 2H); 1.3 (m, 2H); 0.8 (t, J=7 Hz, 3H)

EXAMPLE 9

Synthesis of 6-[(2-butyl-4-chloro-5-hydroxymethyl-1H-imidazol-1-yl)methyl]-2-(2-carboxyphenyl)-4-quinoline-carboxylic acid 50.6 mg (0.0969 mmol) of methyl 6-[(2-butyl-4-chloro-5-hydroxymethyl-1H-imidazol-1-yl)methyl]-2-(2-methoxycarbonylphenyl)-4-quinolinecarboxylate obtained in Example 8 was mixed with 33.5 mg (0.388 mmol) of sodium hydroxide, 1 ml of water and 0.3 ml of ethanol and the mixture was stirred at the room temperature for 24 hours. After concentrated under reduced pressure, the concentrate was partitioned between water and ether. The aqueous layer was acidified with 1N hydrochloric acid and extracted with ethyl acetate to obtain 44.2 mg of 6-[(2-butyl-4-chloro-5-hydroxymethyl-1H-imidazol-1-yl)methyl]-2-(2-carboxyphenyl)-4-quinolinecarboxylic acid. NMR (270 MHz, $CD_3OD$):

δ 7.6–8.6 (m, 8H); 5.6 (s, 2H); 4.6 (s, 2H); 2.7 (t, J=8 Hz, 2H); 1.6 (m, 2H); 1.4 (m, 2H); 0.9 (m, 3H)

EXAMPLE 10

In 15 ml of water were dissolved 14.7 g (0.1 mol) of isatin and 8 g (0.2 mol) of sodium hydroxide. Then, 16.4 g (0.1 mol) of 2-acetylbenzoic acid was added thereto and the resulting mixture was heated at 90° C. under reflux. When the reaction became mild, the mixture was heated at 115° C. for an additional 1 hour. After allowing to cool to room temperature, it was poured into 300 g of water cooled with ice. The aqueous layer was washed with ether and acidified with 2M hydrochloric acid. The precipitate thus formed was collected by filtration to thereby give 9.85 g of 2-(2-carboxyphenyl)-4-quinolinecarboxylic acid. NMR (270 MHz, $CD_3COCD_3$): δ 7.70–8.70 (m,9H).

EXAMPLE 11

To 1,200 ml of an aqueous solution of 90 g of chloral hydrate were added 1,300 g of sodium sulfate decahydrate and subsequently 300 ml of an aqueous solution containing 54 g of o-methylaniline and 43 ml of conc. hydrochloric acid. After further adding 50 ml of an aqueous solution of 110 g of hydroxyamine hydrochloride, the mixture was heated under reflux for 0.5 hour. Then the reaction mixture was cooled with ice and the crystals thus precipitated were collected by filtration. After air-dried, the precipitate was dissolved in 325 ml of conc. sulfuric acid, previously heated to 50° C., under vigorous stirring at a temperature of 75° C. or below. After the completion of the addition, the mixture was heated at 80° C. for 0.5 hour. After allowing to cool, it was poured onto 3 kg of ice. The crystals thus precipitated were collected by filtration to thereby give 33 g of 7-methylsatin.

The procedure of Example 10 was repeated but using 80.0 g of 7-methylisatin synthesized by the method described above instead of isatin. Thus 14.9 g of 2-(2-carboxyphenyl)-8-methyl-4-quinolinecarboxylic acid was obtained. NMR (270 MHz, $CD_3COCD_3$): δ 7.70–8.50 (m,8H); 2.45 (s,3H).

EXAMPLE 12

The procedure of Example 2 was repeated but using 1.38 g of 3-benzylidenephthalide instead of the 2-acetylbenzoic acid. Thus 1.97 g of 2-(2-carboxyphenyl)-6-methyl-3-phenyl-4-quinolinecarboxylic acid was obtained. NMR (270 MHz, $CD_3COCD_3$): δ 7.3–8.1 (m,12H); 2.68 (s,3H).

EXAMPLE 13

A mixture comprising 57.2 g of tetrachlorophthalic anhydride, 25.0 g of malonic acid and 60 ml of pyridine was stirred at 70° to 75° C. for 1.5 hours. After adding 200 ml of water and 200 ml of conc. hydrochloric acid, the mixture was boiled for 10 minutes. After allowing to cool, the precipitate was collected by filtration and dried. The solid product thus obtained was extracted with 600 ml of hot ether. The extract was concentrated and the residue was recrystallized from dilute ethanol. Thus, 25.2 g of 2-acetyl-3,4,5,6-tetrachlorobenzoic acid was obtained. NMR (270 MHz, $CDCl_3$): δ 2.03 (s,3H), IR (KBr) ν (C=O) 1770 $cm^{-1}$, ν (OH) 3380 $cm^{-1}$.

The procedure of Example 2 was repeated but using 2.45 g of the 2-acetyl-3,4,5,6-tetrachlorobenzoic acid obtained above instead of 2-acetylbenzoic acid. Thus 1.9 g of 2-(2-carboxy-3,4,5,6-tetrachlorophenyl)-6-methyl-4-quinolinecarboxylic acid was obtained. NMR (270 MHz, $CD_3COCD_3$): δ 7.3–8.5 (m,4H); 2.70 (s,3H).

EXAMPLE 14

The procedure of Example 13 was repeated but using 52 g of 3,6-dichlorophthalic anhydride instead of tetrachlorophthalic anhydride. Thus 14.1 g of 2-acetyl-3,6-dichlorobenzoic acid was obtained. The procedure of Example 2 was repeated but using 2.2 g of the 2-acetyl-3,6-dichlorobenzoic acid thus obtained instead of 2-acetylbenzoic acid. Thus 1.5 g of 2-(2-carboxy-3,6-dichlorophenyl)-6-methyl-4-quinolinecarboxylic acid was obtained. NMR (270 MHz, $CD_3COCD_3$): δ 7.5–8.5 (m,6H); 2.68 (s,3H).

EXAMPLE 15

The procedure of Example 13 was repeated but using 62 g of 4,5-dichlorophthalic anhydride instead of tetrachlorophthalic anhydride. Thus 19.5 g of 2-acetyl-4,5-dichlorobenzoic acid was obtained. The procedure of Example 2 was repeated but using 2.32 g of the 2-acetyl-4,5-dichlorobenzoic acid thus obtained instead of 2-acetylbenzoic acid. Thus 1.2 g of 2-(2-carboxy-4,5-dichlorophenyl)-6-methyl-4-quinolinecarboxylic acid was obtained. NMR (270 MHz, $CD_3COCD_3$): δ 7.3–8.7 (m,6H); 2.67 (s,3H).

EXAMPLE 16

The procedure of Example 2 was repeated but using 15.8 g of 4-acetylbenzoic acid instead of 2-acetylbenzoic acid. Thus 8.2 g of 2-(4-carboxyphenyl)-6-methyl-4-quinolinecarboxylic acid was obtained. NMR (270 MHz, $Cd_3COCD_3$): δ 7.70–8.70 (m,8H); 2.69 (s,3H).

EXAMPLE 17

Four ml of carbon tetrachloride were added to 540 mg of methyl 2-(2-methoxycarbonylphenyl)-6-methyl-4-quinolinecarboxylate obtained by the method described in the first stage of Example 3. Further, 315 mg of N-bromosuccinimide and 8.7 mg of azobisisobutyronitrile were added thereto and the resulting mixture was heated under reflux for 1 hour. The mixture was concentrated under reduced pressure and the residue was dissolved in dichloromethane and washed with water. The organic layer was dried over magnesium sulfate and filtered. Then the filtrate was concentrated under reduced pressure.

The residue thus obtained was dissolved in 2 ml of N,N-dimethylformamide. After adding 52 mg of 2-ethyl-5,7-dimethyl-3H-imidazo[4,5-b]pyridine and 8.3 mg of sodium hydride, the mixture was stirred at room temperature. Then the mixture was filtered and the filtrate was concentrated under reduced pressure. The resulting residue was purified by flash chromatography on silica gel with the use of a solvent mixture of hexane/ethyl acetate (5:1 to 4:1) to give thereby 44 mg of methyl 6-(2-ethyl-5,7-dimethyl-3H-imidazo|4,5-b|pyridin-3-yl)methyl-2-(2-methoxycarbonylphenyl)-4-quinolinecarboxylate. NMR (270 MHz, CDCl$_3$): δ 7.5–8.5 (m,8H); 7.0 (s,1H); 5.8 (s,2H); 4.0 (s,3H); 3.6 (s,3H); 2.7 (q,J=8Hz,2H); 2.7 (s,3H); 2.6 (s,3H); 1.7 (t,J=8Hz,3H).

The procedure of Example 9 was repeated but using 44 mg of the methyl 6-(2-ethyl-5,7-dimethyl-3H-imidazo-|4,5-b|pyridin-3-yl)methyl-2-(2-methoxycarbonylphenyl)-4-quinolinecarboxylate obtained above instead of the methyl 6-(2-butyl-4-chloro-5-hydroxymethyl-1H-imidazol-1-yl)methyl-2-(2-methoxycarbonylphenyl)-4-quinolinecarboxylate to give thereby 18 mg of 6-(2-ethyl-5,7-dimethyl-3H-imidazo|4,5-b|pyridin-3-yl)methyl-2-(2-carbonylphenyl)-4-quinolinecarboxylic acid. NMR (270 MHz, CDCl$_3$) δ 7.5–8.5 (m,8H); 7.0 (s,1H); 5.7 (s,2H); 2.8 (q,J=8Hz,2H); 2.7 (s,3H); 2.6 (s,3H); 1.7 (t,J=8Hz,3H).

EXAMPLE 18

Ten g of the 2-(2-carboxyphenyl)-4-quinoline-carboxylic acid obtained in Example 10 was dissolved in 200 ml of quinoline. After adding 5 ml of conc. sulfuric acid, the mixture was heated at 160° C. for 1 hour. Then the reaction mixture was poured into water, made alkaline by adding sodium carbonate and washed with toluene. The aqueous layer was neutralized with 3M hydrochloric acid until a precipitate was formed. Then the precipitate was collected by filtration to give thereby 5.1 g of 2-(quinolin-2-yl)benzoic acid. NMR (270 MHz, CD$_3$OD): δ 7.58–8.32 (m,10H).

EXAMPLE 19

In 1 ml of N,N-dimethylacetamide was dissolved 0.2 g of the 2-(2-carboxyphenyl)-6-methyl-4-quinolinecarboxylic acid obtained in Example 2 and heated at 180° C. for 1 hour. Then the reaction mixture was poured into water, made alkaline by adding sodium carbonate and washed with dichloromethane. The aqueous layer was neutralized with 3M hydrochloric acid until a precipitate was formed. After extracting with dichloromethane, 60 mg of 2-(6-methylquinolin-2-yl)benzoic acid was obtained. NMR (270 MHz, CD$_3$OD): δ 7.58–8.32 (m,9H); 2.58 (s,3H).

EXAMPLE 20

Five g of the 2-(2-carboxyphenyl)-6-methyl-4-quinolinecarboxylic acid obtained in Example 2 was dissolved in 10 ml of quinoline. After adding 20 mg of conc. sulfuric acid, the mixture was heated at 160° C. for 1 hour. Then the reaction mixture was poured into water, made alkaline by adding sodium carbonate and washed with toluene. The aqueous layer was neutralized with 3M hydrochloric acid until a precipitate was formed and the precipitate was collected by filtration to give thereby 3.94 g of 2-(6-methylquinolin-2-yl)benzoic acid. NMR (270 MHz, CD$_3$OD): δ 7.58–8.32 (m,9H); 2.58 (s,3H).

EXAMPLE 21

To 1 ml of diphenyl ether were added 0.2 g of the 2-(2-carboxyphenyl)-6-methyl-4-quinolinecarboxylic acid obtained in Example 2. After adding 123 mg of p-toluenesulfonic acid, the mixture was heated at 160° C. for 1 hour. Then the reaction mixture was poured into water, made alkaline by adding sodium hydroxide and washed with ethyl acetate. The aqueous layer was neutralized with 3M hydrochloric acid until a precipitate was formed. After extracting with ethyl acetate, 80 mg of 2-(6-methylquinolin-2-yl)benzoic acid were obtained. NMR (270 MHz, CD$_3$OD): δ 7.58–8.32 (m,9H); 2.58 (s,3H).

EXAMPLE 22

To 3 ml of diphenyl ether were added 0.5 g of the 2-(2-carboxyphenyl)-6-methyl-4-quinolinecarboxylic acid obtained in Example 2. After adding 6.5 mg of copper oxide, the mixture was heated at 170° C. for 1 hour. Then the reaction mixture was poured into water, made alkaline by adding sodium hydroxide and washed with ethyl acetate. The aqueous layer was neutralized with 3M hydrochloric acid until a precipitate was formed. After extracting with ethyl acetate, 0.2 g of 2-(6-methylquinolin-2-yl)benzoic acid were obtained. NMR (270 MHz, CD$_3$OD): δ 7.58–8.32 (m,9H); 2.58 (s,3H).

EXAMPLE 23

In 5 ml of quinoline was dissolved 0.1 g of the 2-(2-carboxyphenyl)-8-methyl-4-quinolinecarboxylic acid obtained in Example 11 and the solution was heated at 170° C. for 1.5 hours. Then the reaction mixture was poured into water, made alkaline by adding sodium hydroxide and washed with toluene. The aqueous layer was neutralized with 3M hydrochloric acid until a precipitate was formed. After extracting with dichloromethane, 0.05 g of 2-(8-methylquinolin-2-yl)benzoic acid were obtained. NMR (270 MHz, CD$_3$OD): δ 7.5–8.3 (m,9H); 2.63 (s,3H).

EXAMPLE 24

One g of the 2-(2-carboxyphenyl)-6-methyl-3-phenyl-4-quinolinecarboxylic acid obtained in Example 12 was dissolved in 20 ml of quinoline. After adding 200 mg of conc. sulfuric acid, the mixture was heated at 170° C. for 1 hour. Then the reaction mixture was poured into water, made alkaline by adding sodium carbonate and washed with toluene. The aqueous layer was neutralized with 3M hydrochloric acid until a precipitate was formed and the precipitate was collected by filtration to give thereby 0.6 g of 2-(6-methyl-3-phenyl-quinolin-2-yl)benzoic acid. NMR (270 MHz, CD$_3$OD): δ 7.5–8.3 (m,13H); 2.57 (s,3H).

EXAMPLE 25

One g of the 2-(2-carboxy-3,4,5,6-tetrachlorophenyl)-6-methyl-4-quinolinecarboxylic acid obtained in Example 13 was dissolved in 15 ml of quinoline. After adding 200 mg of conc. sulfuric acid, the mixture was heated at 160° C. for 1 hour. Then the reaction mixture was poured into water, made alkaline by adding sodium carbonate and washed with toluene. The aqueous layer was neutralized with 3M hydrochloric acid until a precipitate was formed and the precipitate was collected by filtration to give thereby 0.6 g of 2-(6-methylquinolin-2-yl)-3,4,5,6-tetrachlorobenzoic acid. NMR (270 MHz, CD$_3$OD): δ 7.3–8.3 (m,5H); 2.61 (s,3H).

EXAMPLE 26

One g of the 2-(2-carboxy-3,6-dichlorophenyl)-6-methyl-4-quinolinecarboxylic acid obtained in Example 14 was dissolved in 15 ml of quinoline. After adding 250 mg of conc. sulfuric acid, the mixture was heated at 160° C. for 1 hour. Then the reaction mixture was poured into water, made alkaline by adding sodium carbonate and washed with toluene. The aqueous layer was neutralized with 3M hydrochloric acid until a precipitate was formed and the precipitate was collected by filtration to give thereby 0.55 g of 2-(6-methylquinolin-2-yl)-3,6-dichlorobenzoic acid. NMR (270 MHz, CD$_3$OD): δ 7.3–8.3 (m,7H); 2.60 (s,3H).

EXAMPLE 27

One g of the 2-(2-carboxy-4,5-dichlorophenyl)-6-methyl-4-quinolinecarboxylic acid obtained in Example 15 was dissolved in 15 ml of quinoline. After adding 250 mg of conc. sulfuric acid, the mixture was heated at 160° C. for 1.5 hours. Then the reaction mixture was poured into water, made alkaline by adding sodium carbonate and washed with toluene. The aqueous layer was neutralized with 3M hydrochloric acid until a precipitate was formed and the precipitate was collected by filtration to give thereby 0.57 g of 2-(6-methylquinolin-2-yl)-4,5-dichlorobenzoic acid. NMR (270 MHz, CD$_3$OD): δ 7.3–8.3 (m,7H); 2.58 (s,3H).

EXAMPLE 28

In 5 ml of quinoline was dissolved 0.1 g of the 2-(4-carboxyphenyl)-6-methyl-4-quinolinecarboxylic acid obtained in Example 16 and solution was heated at 170° C. for 0.5 hour. Then the reaction mixture was poured into water, made alkaline by adding sodium carbonate and washed with toluene. The aqueous layer was neutralized with 3M hydrochloric acid until a precipitate was formed. After extracting with dichloromethane, 0.06 g of 4-(6-methylquinolin-2-yl)benzoic acid were obtained. NMR (270 MHz, CD$_3$OD): δ 7.5–8.3 (m,9H); 2.56 (s,3H).

EXAMPLE 29

In 10 ml of quinoline were dissolved 44.2 mg of the 6-[(2-butyl-4-chloro-5-hydroxymethyl-1H-imidazol-1-yl)methyl]-2-(2-carboxyphenyl)-4-quinolinecarboxylic acid obtained in Example 9. After adding 100 mg of conc. sulfuric acid, the mixture was heated at 170° C. for 1 hour. Then the reaction mixture was poured into water, made alkaline by adding sodium carbonate and washed with toluene. The aqueous layer was neutralized with 3M hydrochloric acid until a precipitate was formed. Then the precipitate was collected by filtration and purified by flash chromatography on silica gel with the use of chloroform/methanol. Thus 25 mg of 2-{6-[(2-butyl-4-chloro-5-hydroxymethyl-1H-imidazol-1-yl)methyl]quinolin-2-yl}benzoic acid were obtained. NMR (270 MHz, CDCl$_3$): δ 7.2–8.2 (m,9H); 5.4 (s,2H); 4.5 (s,2H); 2.6 (t,J=8Hz,2H); 1.2–1.8 (m,4H); 1.4 (m,2H); 0.8 (t,J=8Hz,3H).

EXAMPLE 30

Eighteen mg of the 6-(2-ethyl-5,7-dimethyl-3H-imidazo[4,5-b]pyridin-3-yl)methyl-2-(2-carboxyphenyl)-4-quinolinecarboxylic acid obtained in Example 17 were dissolved in 5 ml of quinoline. After adding 0.5 ml of conc. sulfuric acid, the mixture was heated at 170° C. for 1 hour. Then the reaction mixture was poured into water, made alkaline by adding sodium carbonate and washed with toluene. The aqueous layer was neutralized with 3M hydrochloric acid until a precipitate was formed. Then the precipitate was collected by filtration and purified by flash chromatography on silica gel with the use of chloroform/methanol. Thus 12 mg of 2-{6-[(2-ethyl-5,7-dimethyl-3H-imidazo[4,5-b]pyridin-3-yl)methyl]quinolin-2-yl}benzoic acid were obtained. NMR (270 MHz, CDCl$_3$): δ 7.5–8.2 (m,8H); 7.4 (s,1H); 7.0 (s,1H); 5.7 (s,2H); 2.8 (q,J=8Hz,2H); 2.7 (s,3H); 2.6 (s,3H); 1.7 (t,J=8Hz,3H).

EXAMPLE 31

Synthesis of 2-propanoylbenzoic acid

Twenty g (136 mmol) of phthalic anhydride, 35 ml (270 mmol) of propionic anhydride and 2.6 g (28 mmol) of sodium propionate were heated at 80° C. with stirring for 45 minutes. After allowing to cool, the reaction mixture was poured into a 10% aqueous solution of acetic acid. The solid matter thus precipitated was collected by filtration and recrystallized from ethanol. The solid product thus obtained was dissolved in 20 ml of a 1.5N aqueous solution of sodium hydroxide and heated under reflux for 3 hours. After allowing to cool, the reaction mixture was acidified with 20% hydrochloric acid and extracted with methylene chloride. The organic layer was dried over magnesium sulfate, filtered and concentrated under reduced pressure to give thereby 6.4 g (36 mmol) of 2-propanoylbenzoic acid. NMR (270 MHz, CDCl$_3$): δ 7.5–8.0 (m,4H); 3.95 (q,J=9.3Hz,2H); 1.38 (t,J=9.3Hz,3H).

EXAMPLE 32

Synthesis of 3-[(4-nitrophenyl)methyl]-2-butyl-3H-imidazo[4,5-b]pyridine

In 550 ml of N,N-dimethylformamide were dissolved 18.3 g (104 mmol) of 2-butyl-1H-imidazo[4,5-b]pyridine and the resulting mixture was added to a 60% aqueous solution of 4.58 g (115 mmol) of sodium hydroxide. After stirring for 30 minutes, 25 g (116 mmol) of p-nitrobenzyl bromide were added to the solution and the resulting mixture was stirred at room temperature for 16 hours. After concentrating under reduced pressure, the residue was dissolved in 300 ml of ethyl acetate. The organic layer was washed with water, dried over magnesium sulfate and filtered. After concentrating under reduced pressure, the residue was purified by silica gel column chromatography with the use of a solvent mixture (toluene/ethyl acetate 2:1) to give thereby 19.1 g of 3-[(4-nitrophenyl)methyl]-2-butyl-3H-imidazo[4,5-b]pyridine. NMR (270 MHz, CDCl$_3$): δ 8.33 (dd,J=8.3Hz,1H); 8.17 (d,J=8.4 Hz,2H); 8.04 (d,J=8.1Hz,1H); 7.22–7.31 (m,3H); 5.59 (s,2H); 2.79 (t,J=7.3Hz,2H); 1.75–1.86 (m,2H); 1.34–1.48 (m,2H); 0.92 (t,J=7.3 Hz,3H).

EXAMPLE 33

Synthesis of 3-[(4-aminophenyl)methyl]-2-butyl-3H-imidazo[4,5-b]pyridine

In 25 ml of ethanol were dissolved 19.1 g (61.7 mmol) of 3-[(4-nitrophenyl)methyl]-2-butyl-3H-imidazo[4,5-b]pyridine obtained by the method described in Example 32. After adding 1 g of active carbon carrying 5% of palladium, the mixture was stirred in a hydrogen gas atmosphere for 18 hours. After filtering off the insoluble matter through Celite and washing with 100 ml of ethanol, the filtrate was concentrated under reduced pressure to give thereby 15.7 g of 3-[(4-aminophenyl)methyl]-2-butyl-3H-imidazo[4,5-b]pyridine. NMR (270 MHz, CDCl$_3$): δ 8.33 (dd,J=1.35, 4.86Hz,1H); 7.98 (dd,J=1.35,7.83Hz,1H); 7.2 (dd,J=4.86, 7.83Hz,1H); 6.97 (d,J=8.4Hz,2H); 6.58 (d,J=8.4Hz,2H); 5.37 (s,2H); 3.6 (bs,NH$_2$); 2.8 (t,J=7.3Hz,2H); 1.72–1.84 (m,2H); 1.33–1.47 (m,2H); 0.92 (t,J=7.3Hz,3H).

EXAMPLE 34

Synthesis of 5-[(2-butyl-3H-imidazo[4,5-b]pyridin-3-yl)methyl]isatin

Ten g (60.6 mmol) of chloral hydrate were dissolved in 135 ml of water and 135 g of sodium sulfate were added thereto. After further adding 40 ml of a solution of 15.7 g (56.1 mmol) of 3-[(4-aminophenyl)methyl]-2-butyl-3H-imidazo[4,5-b]pyridine obtained by the method described in Example 33 in 4.4N hydrochloric acid and 220 ml of an aqueous solution of 12.3 g (177.4 mmol) of hydroxylamine hydrochloride, the resulting mixture was stirred under reflux for 30 minutes. After allowing to cool to room temperature, the water was removed by decantation and the residue was washed with 150 ml of water cooled with ice. Then the residue was dissolved in 170 ml of a 1.5N solution of sodium hydroxide and neutralized with 2N hydrochloric acid. After filtering, the filtrate was acidified with 2N hydrochloric acid. The precipitate was collected by filtration, washed with water cooled with ice and dried.

The isonitrosoacetanilide thus obtained was added to 30 ml of conc. sulfuric acid at 50° C. for 40 minutes and then heated at 90° C. for 15 minutes. After cooling to room temperature, the mixture was poured into 200 ml of water cooled with ice. The precipitate was collected by filtration and the residue was dried and purified by silica gel column chromatography with the use of ethyl acetate as a solvent to give thereby 8.4 g of 5-[(2-butyl-3H-imidazo[4,5-b]pyridin-3-yl)methyl]isatin. NMR (270 MHz, CD$_3$OD): δ 8.45 (dd, J=1.35,4.86Hz,1H); 8.05 (dd,J=1.35,8.1Hz,1H); 7.51 (d,J= 1.9Hz,1H); 7.42 (dd,J=4.9,8.1Hz,1H); 7.28 (dd,J=1.9, 8.6Hz,1H); 6.76 (d,J=8.6Hz,1H); 5.5 (s,2H); 3.0 (t,J=7.8Hz, 2H); 1.66–1.79 (m,2H); 1.35–1.49 (m,2H); 0.93 (t,J=7.8Hz, 3H).

EXAMPLE 35

Synthesis of 2-(2-carboxyphenyl)-3-methyl-6-[(2-butyl-3H-imidazo[4,5-b]pyridin-3-yl)methyl]-4-quinolinecarboxylic acid In 110 ml of a 1N aqueous solution of sodium hydroxide were dissolved 6.4 g (36 mmol) of 2-propanoylbenzoic acid obtained by the method described in Example 31. Then 9.4 g (36 mmol) of 5-(2-butyl-3H-imidazo[4,5-b]pyridin-3-yl) methylisatin obtained by the method described in Example 33 were added thereto and the mixture was heated under reflux for 4 hours. After adding 100 ml of water and washing with 100 ml of methylene chloride, the aqueous layer was acidified with 2N hydrochloric acid under stirring and ice-cooling. The precipitate was collected by filtration and dried to give thereby 14.2 g of 2-(2-carboxyphenyl)-3-methyl-6-[(2-butyl-3H-imidazo[4,5-b]pyridin-3-yl)methyl]-4-quinolinecarboxylic acid. NMR (270 MHz, CD$_3$COCD$_3$): δ 9.2 (m,1H); 8.2–8.7 (m,3H); 7.83 (d,J=7.8Hz,1H); 7.4–7.9 (m,5H); 5.74 (s,2H); 3.5 (s,3H); 2.88 (t,J=7.8Hz,2H); 2.64 (s,3H); 1.81–1.89 (m,2H); 1.38–1.45 (m,2H); 0.9 (t, J=7.3Hz,3H).

EXAMPLE 36

Synthesis of methyl 2-(2-methoxycarboxyphenyl)-3-methyl-6-[(2-butyl-3H-imidazo[4,5-b]pyridin-3-yl)methyl]-4-quinolinecarboxylate Five g (10 mmol) of 2-(2-carboxyphenyl)-3-methyl-6-[(2-butyl-3H-imidazo[4,5-b]pyridin-3-yl)methyl]-4-quinolinecarboxylic acid obtained by the method described in Example 35 was dissolved in 50 ml of methanol and the resulting mixture was added dropwise to 1.6 ml (22 mmol) of thionyl chloride under ice-cooling. After heated under reflux for 4 hours, the mixture was cooled to room temperature and methanol was distilled off. Fifty ml of water were added to the residue, which was neutralized with a saturated sodium bicarbonate solution and extracted with 100 ml of ethyl acetate. The organic layer was dried over magnesium sulfate followed by filtration. The resulting filtrate was concentrated and the residue was purified by flash chromatography on silica gel with the use of a solvent mixture of hexane/ethyl acetate (1:1) to give 3.6 g of methyl 2-(2-methoxycarboxyphenyl)-3-methyl-6-[(2-butyl-3H-imidazo[4,5-b]pyridin-3-yl)methyl]-4-quinolinecarboxylate. NMR (270 MHz, CDCl$_3$): δ 8.3 (m, 1H); 8.0–8.1 (m,3H); 7.79 (d,J=7.8Hz,1H); 7.1–7.6 (m,5H); 5.71 (s,2H); 3.5 (s,3H); 2.87 (t,J=7.8Hz,2H); 2.6 (s,3H); 1.80–1.88 (m,2H); 1.4–1.48 (m,2H); 0.92 (t,J=7.3Hz,3H).

EXAMPLE 37

Synthesis of 2-(2-methoxycarboxyphenyl)-3-methyl-6-[(2-butyl-3H-imidazo[4,5-b]pyridin-3-yl)methyl]-4-quinolinecarboxylic acid In 35 ml of methanol were dissolved 3.6 g (6.9 mmol) of methyl 2-(2-methoxycarboxyphenyl)-3-methyl-6-[(2-butyl-3H-imidazo[4,5-b]pyridin-3-yl)methyl]-4-quinolinecarboxylate obtained in the method described in Example 36. Then, 14 ml of a 0.5N aqueous solution of sodium hydroxide were added thereto and the mixture was stirred at room temperature for 16 hours. After the reaction mixture was neutralized with 1N hydrochloric acid, methanol was distilled off and 35 ml of water were added to the residue. The mixture was extracted with 30 ml of methylene chloride and the aqueous layer was acidified with 2N hydrochloric acid under stirring. The resulting precipitate was collected by filtration, washed with water and dried to give 1.8 g of 2-(2-methoxycarboxyphenyl)-3-methyl-6-[(2-butyl-3H-imidazo[4,5-b]pyridin-3-yl)methyl]-4-quinolinecarboxylic acid. NMR (270 MHz, CDCl$_3$) δ 8.3 (m,1H); 8.0–8.1 (m,3H); 7.79 (d,J=7.8Hz,1H); 7.1–7.6 (m,5H); 5.71 (s,2H); 3.5 (s,3H); 2.87 (t,J=7.8Hz,2H); 2.6 (s,3H); 1.80–1.88 (m,2H); 1.4–1.48 (m,2H); 0.92 (t,J=7.3Hz,3H).

EXAMPLE 38

Synthesis of methyl 2-{3-methyl-6-[(2-butyl-3H-imidazo[4,5-b]pyridin-3-yl)methyl]}quinolin-2-yl}benzoate In 18 ml of diphenyl ether were suspended 1.8 g (3.5 mmol) of 2-(2-methoxycarboxyphenyl)-3-methyl-6-[(2-butyl-3H-imidazo[4,5-b]pyridin-3-yl)methyl]-4-quinolinecarboxylic acid obtained by the method described in Example 37 and the mixture was heated at 185° C. for 1 hour. After allowing to cool to room temperature, the mixture was purified by flash chromatography on silica gel with the use of a solvent mixture of hexane/ethyl acetate (1:1) to give 0.97 g of methyl 2-{3-methyl-6-[(2-butyl-3H-imidazo[4,5-b]pyridin-3-yl)methyl]}quinolin-2-yl}benzoate. NMR (270 MHz, CD$_3$OD): δ 8.3 (m,1H); 8.0–8.1 (m,3H); 7.79 (d,J=7.8Hz,1H); 7.1–7.6 (m,6H); 5.71 (s,2H); 3.5 (s,3H); 2.87 (t,J=7.8Hz,2H); 2.6 (s,3H); 1.80–1.88 (m,2H); 1.4–1.48 (m,2H); 0.92 (t,J=7.3Hz,3H).

EXAMPLE 39

Synthesis of 3-[(4-nitrophenyl)methyl]-5,7-dimethyl-2-ethyl-3H-imidazo[4,5-b]pyridine The procedure of Example 32 was repeated but using 200 mg of 5,7-dimethyl-2-ethyl-1H-imidazo[4,5-b]pyridine in place of 2-butyl-1H-imidazo[4,5-b]pyridine to give thereby 205 mg of 3-[(4-nitrophenyl)methyl]-5,7-dimethyl-2-ethyl-3H-imidazo[4,5-b]pyridine. NMR (270 MHz, CDCl₃): δ 7.2–8.3 (m,5H); 5.6 (s,2H); 2.8 (qJ=8Hz,2H); 2.7 (s,3H); 2.6 (s,3H); 1.3 (tJ=8Hz,3H).

EXAMPLE 40

Synthesis of 3-[(4-aminophenyl)methyl]-5,7-dimethyl-2-ethyl-3H-imidazo[4,5-b]pyridine Starting from 202 mg of 3-[(4-nitrophenyl)methyl]-5,7-dimethyl-2-ethyl-3H-imidazo[4,5-b]pyridine obtained by the method described in Example 39, the procedure of Example 33 was repeated to give thereby 162 mg of 3-[(4-aminophenyl)methyl]-5,7-dimethyl-2-ethyl-3H-imidazo[4,5-b]pyridine. NMR (270 MHz, CDCl₃): δ 7.0–8.3 (m,4H); 6.6 (s,1H); 5.4 (s,2H); 3.6 (bs,2H); 2.8 (qJ=8Hz,2H); 2.7 (s,3H); 2.6 (s,3H); 1.3 (tJ=8Hz,3H).

EXAMPLE 41

Synthesis of 5-[(5,7-dimethyl-2-ethyl-3H-imidazo[4,5-b]pyridin-3-yl)methyl]isatin Starting from 160 mg of 3-[(4-aminophenyl)methyl]-5,7-dimethyl-2-ethyl-3H-imidazo[4,5-b]pyridine obtained in Example 40, the procedure of Example 34 was repeated to give 84 mg of 5-[(5,7-dimethyl-2-ethyl-3H-imidazo[4,5-b]pyridin-3-yl)methyl]isatin. NMR (270 MHz, CDCl₃): δ 7.3–8.5 (m,4H); 6.8 (s,1H); 5.5 (s,2H); 2.9 (qJ=8Hz,2H); 2.7 (s,3H); 2.6 (s,3H); 1.5 (tJ=8Hz,3H).

EXAMPLE 42

Synthesis of 2-(2-carboxyphenyl)-6-[(5,7-dimethyl-2-ethyl-3H-imidazo[4,5-b]pyridin-3-yl)methyl]-4-quinolinecarboxylic acid By using acetylbenzoic acid and 19 mg of 5-[(5,7-dimethyl-2-ethyl-3H-imidazo[4,5-b]pyridin-3-yl)methyl]isatin obtained in Example 41, the procedure of Example 35 was repeated to give thereby 27 mg of 2-(2-carboxyphenyl)-6-[(5,7-dimethyl-2-ethyl-3H-imidazo[4,5-b]pyridin-3-yl)methyl]-4-quinolinecarboxylic acid. NMR (270 MHz, CDCl₃): δ 7.4–8.2 (m,8H); 7.0 (s,1H); 5.7 (s,2H); 2.8 (qJ=8Hz,2H); 2.7 (s,3H); 2.6 (s,3H); 1.7 (tJ=8Hz,3H).

All references cited herein are incorporated by reference herein in entirety.

While the invention has been described in detail and with reference to specific examples thereof, it will be apparent to one skilled in the art that various changes and modifications can be made therein without departing from the spirit and scope thereof.

What is claimed is:

1. A process for producing quinolin-2-yl benzoic acids comprising decarboxylating 2-(carboxyphenyl)-4-quinolinecarboxylic acids in which a carboxyl group bonded to a phenyl group is esterified, while a carboxyl group bonded to a quinoline ring is not esterified, and both rings may have one or more substituents inert to the decarboxylation reaction.

2. The process of claim 1, wherein said decarboxylation is performed in an inert solvent in the presence of an acid at a temperature of 100° to 250° C.

3. The process of claim 1, wherein said 2-(carboxyphenyl)-4-quinolinecarboxylic acid is 2-(2-alkoxycarbonylphenyl)-6-methyl-4-quinolinecarboxylic acid.

4. The process of claim 1, wherein said 2-(carboxyphenyl)-4-quinolinecarboxylic acid is a compound of formula (1a) and said quinolin-2-yl benzoic acid is a compound of formula (2a):

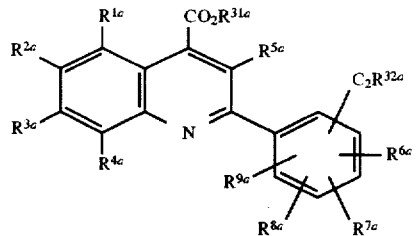

Formula 1a

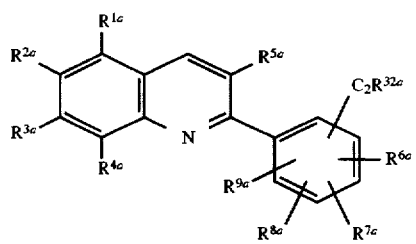

Formula 2a wherein $R^{1a}$, $R^{3a}$, $R^{4a}$, $R^{5a}$, $R^{6a}$, $R^{7a}$, $R^{8a}$ and $R^{9a}$ each independently is a hydrogen atom, a halogen atom, a lower alkyl group, a cyclo lower alkyl group, an aryl group, an aralkyl group, an alkoxy group or —$C_mF_{2m+1}$; $R^{2a}$ is a lower alkyl group, a cyclo lower alkyl group, an aryl group, an aralkyl group, an alkoxy group, —$C_nF_{2n+1}$ or —$CH_2Q$, wherein Q is a monovalent organic group derived from an organic compound having an —NH-group by eliminating the hydrogen atom bonded to said nitrogen atom; $R^{31a}$ is a hydrogen atom; $R^{32a}$ is a hydrogen atom, a lower alkyl group, an alkenyl group, a cyclo lower alkyl group, an aryl group or an aralkyl group; and m and n each independently is an integer of from 1 to 6.

5. The process of claim 4, wherein $R^{1a}$, $R^{3a}$, $R^{4a}$, $R^{5a}$, $R^{6a}$, $R^{7a}$, $R^{8a}$ and $R^{9a}$ each independently is a hydrogen atom, a halogen atom or a lower alkyl group; $R^{2a}$ is a hydrogen atom, a lower alkyl group or —$CH_2Q$; —$COOR^{32a}$ is located at the 2-position of the benzene ring; and $R^{32a}$ is a lower alkyl group.

6. The process of claim 4, wherein Q is a substituted 1H-imidazol-1-yl group or a substituted 3H-imidazo[4,5-b]pyridin-3-yl group.

7. A process for producing a 2-(carboxyphenyl)-4-quinolinecarbvoxylic acid of formula (1a):

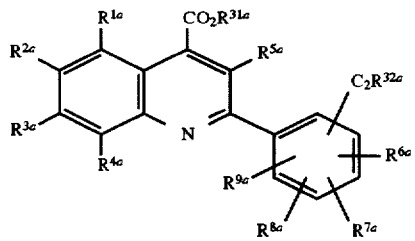

Formula 1a comprising reacting an isatin of formula (5a):

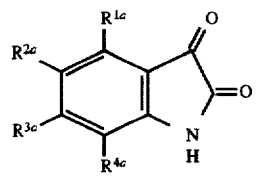

Formula 5a with an acylbenzoic acid of formula (6a):

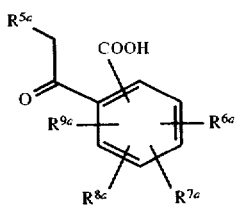

Formula 6a wherein $R^{1a}$, $R^{3a}$, $R^{4a}$, $R^{5a}$, $R^{6a}$, $R^{7a}$, $R^{8a}$ and $R^{9a}$ each independently is a hydrogen atom, a halogen atom, a lower alkyl group, a cyclo lower alkyl group, an aryl group, an aralkyl group, an alkoxy group or —$C_mF_{2m+1}$; $R^{2a}$ is —$CH_2Q$, wherein Q is a monovalent organic group derived from an organic compound having an —NH-group by eliminating the hydrogen atom bonded to said nitrogen atom; $R^{31a}$ and $R^{32a}$ each independently is a hydrogen atom, a lower alkyl group, an alkenyl group, a cyclo lower alkyl group, an aryl group or an aralkyl group; and m is an integer of from 1 to 6.

8. The process of claim 7, wherein $R^{1a}$, $R^{3a}$, $R^{4a}$, $R^{5a}$, $R^{6a}$, $R^{7a}$, $R^{8a}$ and $R^{9a}$ each independently is a hydrogen atom, a halogen atom or a lower alkyl group; $R^{2a}$ is a lower alkyl group or —$CH_2Q$; —$COOR^{32a}$ is located at the 2-position of the benzene ring; and $R^{31a}$ and $R^{32a}$ each independently is a hydrogen atom or a lower alkyl group.

9. The process of claim 7, wherein Q is a substituted 1H-imidazol-1-yl group or a substituted 3H-imidazo[4,5-b]pyridin-3-yl group.

10. A process for producing quinolin-2-yl benzoic acids comprising decarboxylating 2-(carboxyphenyl)-4-quinolinecarboxylic acids in which a carboxyl group bonded to a phenyl group and a carboxyl group bonded to a quinoline ring are not esterified, and both rings may have one or more substituents inert to the decarboxylation reaction.

11. The process of claim 10, wherein said decarboxylation is performed in an inert solvent in the presence of an acid at a temperature of 100° to 250° C.

12. The process of claim 10, wherein said 2-(carboxyphenyl)-4-quinolinecarboxylic acid is 2-(2-carboxy-phenyl)-6-methyl-4-quinolinecarboxylic acid.

13. The process of claim 10, wherein said 2-(carboxyphenyl)-4-quinolinecarboxylic acid is a compound of formula (1a) and said quinolin-2-yl benzoic acid is a compound of formula (2a):

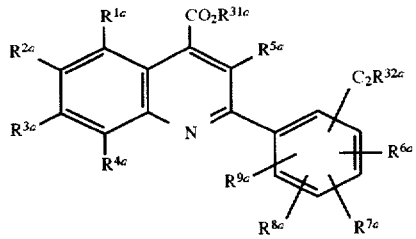

Formula 1a

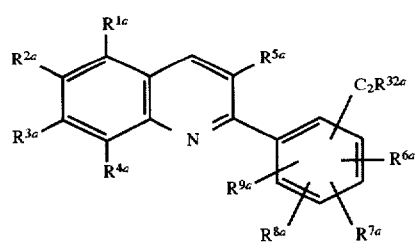

Formula 2a wherein $R^{1a}$, $R^{3a}$, $R^{4a}$, $R^{5a}$, $R^{6a}$, $R^{7a}$, $R^{8a}$ and $R^{9a}$ each independently is a hydrogen atom, a halogen atom, a lower alkyl group, a cyclo lower alkyl group, an aryl group, an aralkyl group, an alkoxy group or —$C_mF_{2m+1}$; $R^{2a}$ is a hydrogen atom, a halogen atom, a lower alkyl group, a cyclo lower alkyl group, an aryl group, an aralkyl group, an alkoxy group, —$C_nF_{2n+1}$ or —$CH_2Q$, wherein Q is a monovalent organic group derived from an organic compound having an —NH-group by eliminating the hydrogen atom bonded to said nitrogen atom; $R^{31a}$ is a hydrogen atom; $R^{32a}$ is a hydrogen atom; and m and n each independently is an integer of from 1 to 6.

14. The process of claim 13, wherein $R^{1a}$, $R^{3a}$, $R^{4a}$, $R^{5a}$, $R^{6a}$, $R^{7a}$, $R^{8a}$ and $R^{9a}$ each independently is a hydrogen atom, a halogen atom or a lower alkyl group; $R^{2a}$ is a hydrogen atom, a lower alkyl group or —$CH_2Q$; and —$COOR^{32a}$ is located at the 2-position of the benzene ring.

15. The process of claim 13, wherein Q is a substituted 1H-imidazol-1-yl group or a substituted 3H-imidazo[4,5-b]pyridin-3-yl group.

\* \* \* \* \*